United States Patent [19]

Austin et al.

[11] Patent Number: 5,410,906

[45] Date of Patent: May 2, 1995

[54] METHOD FOR DETERMINING DAMPING COEFFICIENTS

[75] Inventors: Stephen A. Austin, Amston; Andrew J. Hull, New London; David A. Hurdis, Old Saybrook; Kent D. Kasper, Old Lyme, all of Conn.

[73] Assignee: The United States of America as represented by the Secretary of the Navy, Washington, D.C.

[21] Appl. No.: 152,635

[22] Filed: Oct. 27, 1993

[51] Int. Cl.$^6$ .................... G01M 19/00; G01D 17/04
[52] U.S. Cl. .................... 73/11.04; 73/12.01
[58] Field of Search .............. 73/11.04, 12.01, 12.09

[56] References Cited

U.S. PATENT DOCUMENTS 5,025,655  6/1991  Umemura et al. .............. 73/12.09

FOREIGN PATENT DOCUMENTS 57-094148  6/1982  Japan .................... 73/11.04

Primary Examiner—Hezron E. Williams
Assistant Examiner—Michael J. Brock
Attorney, Agent, or Firm—Michael J. McGowan; Prithvi C. Lall; Michael F. Oglo

[57] ABSTRACT

There is disclosed a method for determining damping coefficients, the method including the steps of providing a damper assembly including a bar of known parameters, and a viscous damper, wherein a first end of the bar is disposed in the viscous damper while the second end of the bar is free, applying a known force to the second end of the bar in a direction toward the first end of the bar, measuring the response function of the assembly, comprising the ratio of the bar acceleration to the applied force, determining the eigenvalues of the response function, and from the eigenvalues computing the damping coefficient of the damper assembly.

3 Claims, 3 Drawing Sheets

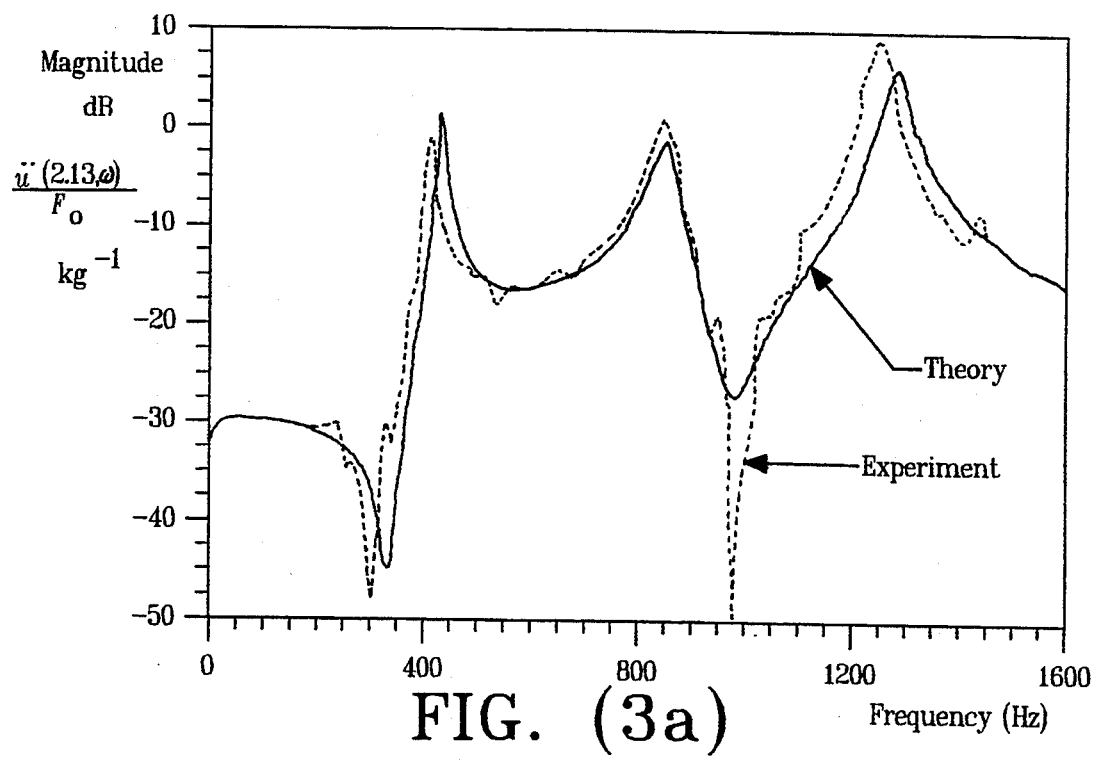
FIG. (3a)
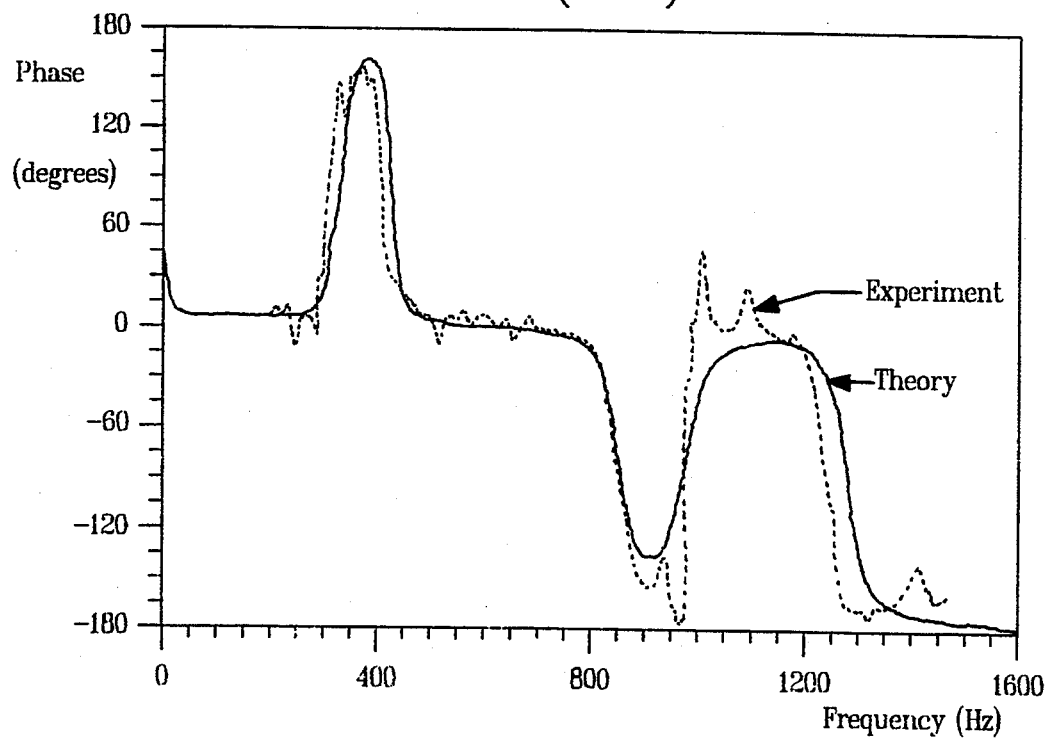
FIG. (3b)

METHOD FOR DETERMINING DAMPING COEFFICIENTS

STATEMENT OF GOVERNMENT INTEREST

The invention described herein may be manufactured and used by or for the Government of the United States of America for governmental purposes without payment of any royalties thereon or therefor.

BACKGROUND OF THE INVENTION (1) Field of the Invention

This invention relates to measurement methods and is directed more particularly to a method for determining damping coefficients of viscous dampers.

(2) Description of Prior Art

The measurement of system mass, damping, and stiffness coefficients is a classical engineering problem that has been addressed by a number of researchers. Their methods typically consist of measuring a frequency response function (transfer function) of a system and then curve fitting a multidegree of freedom model to the magnitude and phase angle of the system response. During this approximation process, the system parameters are identified. The measurement of the mass and stiffness coefficients is usually straightforward. The inclusion of damping into a system produces a bounded complex system response, and thus the extraction of these damping characteristics is more complicated. Since the damping coefficients are usually small in magnitude compared with the system stiffness and mass parameters, the estimation (or measurement) of the damping coefficients frequently has been inaccurate.

Accordingly, there is a need for a method by which damping coefficients may be determined accurately.

SUMMARY OF THE INVENTION

It is, therefore, an object of the invention to provide a method for direct measurement of the damping coefficient of a viscous damper.

With the above and other objects in view, as will hereinafter appear, a feature of the present invention is the provision of a method for determining damping coefficients, the method including the steps of providing a damper assembly including a bar of known length [L, in meters (m)], cross-sectional area (A, in m$^2$), density [$\rho$, in kilograms per meters cubed (kg/m$^3$)] and modulus of elasticity [E, in Newtons/m$^2$(N/m$^2$)] and a viscous damper, wherein a first end of the bar is mounted in the viscous damper while leaving the second end of the bar free, applying a known force (F, in N) to the second end of the bar in a direction toward the first end of the bar, measuring the response function of the assembly, the response function comprising the ratio of the bar acceleration to the applied force, determining the eigenvalues of the response function, and computing the damping coefficient [c, in Newton seconds/m (N-sec/m)], of the viscous damper in accordance with the formula:

$$c = \frac{AE}{s}\left\{\frac{1 - \exp\left\{\frac{2L}{s} Re(\Lambda_n)\right\}}{1 + \exp\left\{\frac{2L}{s} Re(\Lambda_n)\right\}}\right\}$$

wherein s is the longitudinal wave speed in the bar (m/sec) and $\Lambda_n$ is the eigenvalue. The above and other features of the invention will now be more particularly described with reference to the accompanying drawings and pointed out in the claims. It will be understood that the particular method embodying the invention is shown by way of illustration only and not as a limitation of the invention. The principles and features of this invention may be employed in various and numerous embodiments without departing from the scope of the invention.

BRIEF DESCRIPTION OF THE DRAWINGS

Reference is made to the accompanying drawings in which is shown an illustrative embodiment of the invention, from which its novel features and advantages will be apparent.

In the drawings:

FIGS. 3(a) and 3(b) are illustrative of transfer function of acceleration response divided by force input versus frequency at x=2.13 meters.

DESCRIPTION OF THE PREFERRED EMBODIMENT

The inventive method disclosed herein finds application in the determination of frequency-dependent damping coefficients of one-dimensional damping devices. This technique relies on the theoretical formulation of the eigenfunctions and eigenvalues of a longitudinal bar with free-end and damped-end boundary conditions. The eigenvalues are complex functions dependent on the damping coefficient at the boundary, the length of the bar, the density of the bar, the elastic modulus of the bar, and the cross-sectional area of the bar. The functional form of the eigenvalues can be inverted, such that the damping coefficient at the boundary becomes a function of the real part of the eigenvalue and beam properties of the system. The inversion is useful because the damping coefficient becomes a function of measured quantities. The properties of the bar are well known and can be varied through design, and the eigenvalues can be extracted from a frequency response function (transfer function) of the system.

Figure 1:
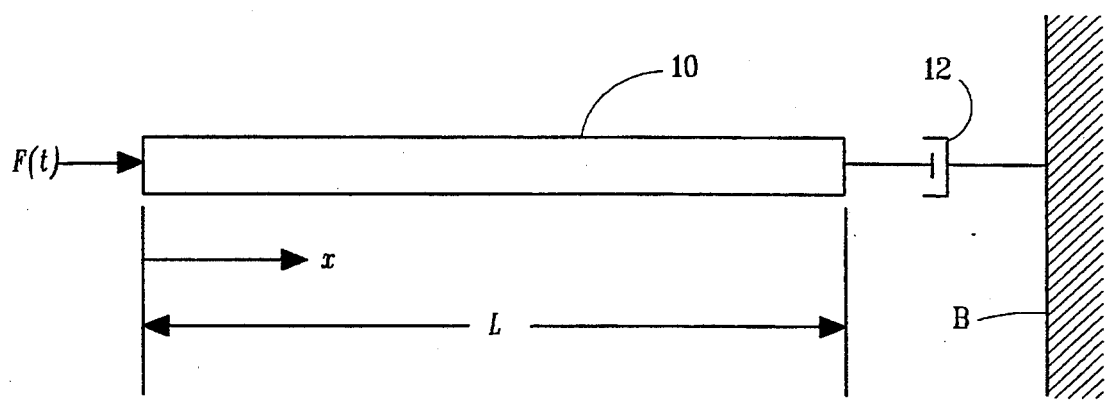
FIG. 1 is a diagrammatical representation of the assembly used in carrying out the inventive method.

Referring to FIG. 1, it will be seen that the one-dimensional axial bar 10 is free at x=0, and connected to a viscous damper 12 at x=L. A force F (t) is applied to the bar at location x=0. The connection of the damper 12 to the bar 10 results in a bounded complex system transfer function (frequency response function, or FRF). The linear second-order wave equation modeling particle displacement in the bar is:

$$\frac{\partial^2 u(x,t)}{\partial t^2} - s^2 \frac{\partial^2 u(x,t)}{\partial x^2} = \frac{\delta(x)F(t)}{\rho A} \quad (1)$$

where u(x,t) is the particle displacement (m), $\rho$ is the density of the bar (kg/m$^3$), s is the longitudinal wave speed in the bar (m/sec), x is the spatial location (m), t is the time (sec), A is the area of the bar (m$^2$), F is applied force (N), and $\delta$ is the Dirac delta function (m$^{-1}$). The wave speed s is equal to the square root of the quantity of the modulus of Elasticity E (N/m$^2$) divided by the density (s=$\sqrt{E/\rho}$). The wave equation assumes a uniform area and negligible internal loss in the bar.

The free boundary at $x=0$ can be modeled as:

$$\frac{\partial u}{\partial x}(0, t) = 0. \tag{2}$$

The boundary condition at $x=L$ is obtained by matching the force at the end of the bar to the viscous dissipative force in the damper. This expression is:

$$AE\frac{\partial u}{\partial x}(L, t) = -c\frac{\partial u}{\partial t}(L, t), \tag{3}$$

where c is the viscous damping coefficient (N-sec/m). When c is equal to zero (or infinity), the boundary at $x=L$ reflects all the wave energy, and the system response is composed only of standing waves. When c is equal to $A\sqrt{\rho E}$, the boundary at $x=L$ absorbs all the wave energy, the system response is composed only of propagating waves. All other values of c exhibit some combination of standing and propagating wave energy in their response.

The eigenvalues of the above-described model are found by applying separation of variables to the homogeneous version of equation (1) and then to the boundary condition in equations (2) and (3). Separation of variables assumes that the solution is a product of a function in the spatial domain multiplied by a function in the time domain:

$$u(x,t)=X(x)T(t). \tag{4}$$

Inserting equation (4) into the homogeneous version of equation (1) produces two independent ordinary differential equations, each with the complex-valued separation constant $\lambda$: namely, $$\frac{d^2X(x)}{dx^2} - \lambda^2 X(x) = 0 \tag{5}$$

and $$\frac{d^2T(t)}{dt^2} - s^2\lambda^2 T(t) = 0. \tag{6}$$

The spatial ordinary differential equation given in equation (5) is solved using the boundary condition of equation (2):

$$X(x)=e^{\lambda x}+e^{-\lambda x}. \tag{7}$$

The time-dependent ordinary differential equation yields the following general solution:

$$T(t)=Ge^{s\lambda t}+He^{-s\lambda t}. \tag{8}$$

Applying the boundary condition of equation (3) to equations (5) and (6) yields $H=0$ and the separation constants $$\lambda_n = \frac{1}{2L}\log_e\left(\frac{AE-cs}{AE+cs}\right) + \frac{n\pi}{L}i \tag{9}$$

$(n = 0, \pm 1, \pm 2, \ldots,)$ and $$\lambda = 0. \tag{10}$$

Figure 2:
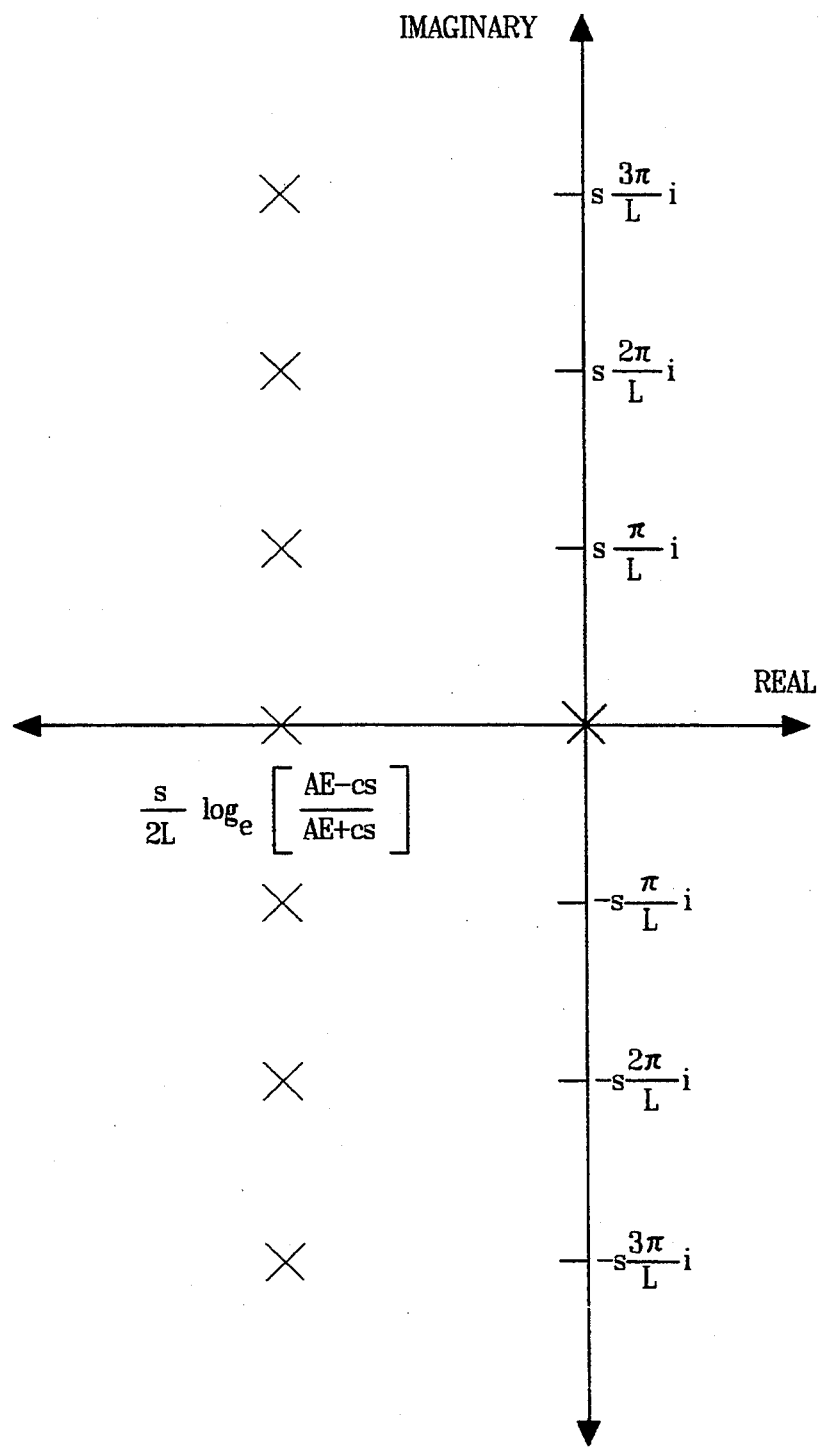
FIG. 2 is a graph illustrative of eigenvalue location in the complex plane.

The eigenvalues $\Lambda_n$, of the system, are equal to the separation constant multiplied by the wave speed s ($\Lambda_n=s\lambda_n$). An eigenvalue plot is shown in FIG. 2. Each of the eigenvalues is a function of the damping at the boundary. When the value of damping at the boundary is increased, the eigenvalues will move to the left in the complex plane. Critical damping for this system occurs when $AE=cs$. The inverse function of equation (9) allows the damping to be computed from the measured eigenvales. Although equation (10), which represents a rigid body mode, is not used in the computation of damping, it must be used when the theoretical transfer function is completed.

The frequency-dependent damping coefficient c at $x=L$ can be determined at each bar resonance from the real component of the eigenvalue at that resonance. The real and imaginary components of the eigenvalves are easily extracted from the measured transfer function, which is the bar response divided by the input force. The computation of damping coefficients begins by multiplying equation (9) by the wave speed, s, and is expressed as $$Re(\Lambda_n) + iI_m(\Lambda_n) = \frac{s}{2L}\log_e\left(\frac{AE-cs}{AE+cs}\right) + s\frac{n\pi}{L}i, \tag{11}$$

where Re( ) denotes the real part, $I_m$ ( ) denotes the imaginary part, and the subscript n denotes the nth resonance. The real-valued terms from equation (11) can be written separately as $$Re(\Lambda_n) = \frac{s}{2L}\log_e\left(\frac{AE-cs}{AE+cs}\right) \tag{12}$$

Multiplying both sides by 2 (L/s) and then taking the exponential of both sides to remove the natural log on the right hand side gives $$\left(\frac{AE-cs}{AE+cs}\right) = \exp\left(\frac{2L}{s}Re(\Lambda_n)\right). \tag{13}$$

Solving for c in equation (13) yields $$c = \frac{AE}{s}\left\{\frac{1-\exp\left(\frac{2L}{s}Re(\Lambda_n)\right)}{1+\exp\left(\frac{2L}{s}Re(\Lambda_n)\right)}\right\}, \tag{14}$$

where c is in units of N-sec/m. The frequency-dependent damping coefficient of the viscous damper can be computed using equation (14) when the eigenvalues at the system resonance are known. Each damping value corresponds to the measured resonant frequency of the bar. Theoretically, when $AE=cs$, the system is critically damped, and the real parts of the eigenvalues are located at negative infinity in the complex plane. Experimentally, this very large damping value is difficult to produce. If this limit could actually be reached, an increase in the bar area would result in a larger critical damping coefficient, which, in turn, would shift the real part of the eigenvalue locations of the system from negative infinity to discrete values. Thus, meaningful calculations of damping values from the measured system eigenvalues would be insured.

EXAMPLE

An experimental apparatus comprised of 6.096 m (20 foot) steel bar attached to a Monroe automotive shock absorber. The bar had a width and height of 0.0254 m (1 inch), which resulted in a cross-sectional area of 0.000645 m² (1 inch²). The shock absorber was tested at the standard installed operational length of 0.457 m (18 inches). The end at x=0 was excited with a Bruel and Kjaer (B&K) Type 8202 modal impact hammer containing a B&K Type 8200 force transducer. The bar acceleration was measure at five locations using a B&K Type 4368 accelerometer. The two signals were input into a Hewlett-Packard 3562 dual channel spectrum analyzer that calculated the system frequency response function. This response function used the accelerometer as the output and the applied force as the input. The analyzer also evaluated the eigenvalues of the response function. The real component of the eigenvalues was used in the above equations to determine the damping in the shock absorber.

Table 1, hereinbelow, shows the mean and standard deviations of the measured eigenvalues for the system. These values were calculated from five sets of measurements at five different locations (x=1.82, 2.13, 2.74, 3.66, and 4.57 m (6, 7, 9, 12, and 15 feet)). Each individual eigenvalue was measured from a transfer function composed of five averaged Fast Fourier transforms. The calculated damping values for the system at the natural frequencies are shown in Table 2. The standard deviations of the eigenvalues at each measured frequency were 4.4, 15.4, and 12.8 percent for the first, second and third resonances, respectively. The minimal deviations indicate the inventive method provides a relatively stable measurement process for the dynamic viscous damping of a device.

The system transfer function can be computed using a modal method that assumes an impulse force input at x=0. This theoretical transfer function is $$\frac{u(x,\omega)}{F_0} = \frac{-\omega^2}{2\rho AL} \sum_{n=-\infty}^{\infty} \frac{\phi_n(x)}{(i\omega - \Lambda_n)\Lambda_n} - \frac{i\omega}{\rho AL} \sum_{n=-\infty}^{\infty} \frac{1}{\Lambda_n}, \quad (15)$$

where ω is the frequency (rad/s), i is the square root of −1, and the eigenfunctions $\phi_n(x)$, given in equation (7), are evaluated using the n-indexed separation constant as $$\phi_n(x) = e^{\lambda_n x} + e^{-\lambda_n x}. \quad (16)$$

A comparison of equation (15) to the experiment is shown in FIGS. 3(a) and 3(b). The solid line is the theoretical transfer function and the dashed line is the experiment at x=2.13 m (7 feet). Here, equation (15) was evaluated using seven terms ((−3≦n≦3), where n is an integer). The transfer function was evaluated by inserting the calculated damping value at each resonance into the theoretical eigenvalue. Because of the symmetry of the problem, the damping values obtained for the positive n modes were used for the corresponding negative n modes. The damping at the n=0 mode was evaluated using the value obtained from the n=1 mode. This process allowed the frequency-dependent characteristic of the damping to be incorporated in to the theoretical transfer function. The 7.2 percent average difference between the theory and the measurement was calculated using the equation $$\% \text{ difference} = \left| \frac{\text{THEORY} - \text{EXPERIMENT}}{\text{MAX(THEORY)}} \right| \cdot 100. \quad (17)$$

This equation allows percentage differences to be calculated while effectively ignoring the nulls of the system transfer function. It should not be used for systems with very low damping because the large magnitudes present will tend to distort differences between data and theory.

Table 3 compares the theoretical imaginary natural frequency to the experimentally measured natural frequency. The percentage differences in this table were calculated using $$\% \text{ difference} = \left| \frac{\text{THEORY} - \text{EXPERIMENT}}{\text{THEORY}} \right| \cdot 100. \quad (18)$$

The comparison between theory and experiment shows substantial agreement. The slight difference between the theoretical and the experimental results is due to the stiffness contribution of the shock absorber to the system. The small percentage difference in Table 3 ensures that the stiffness of the bar is much greater than the stiffness of the damping device, which is required if the damper is to be modeled as a pure loss term.

TABLE 1

| Measured System Mean Eigenvalues and Standard Deviations | | | | |
|---|---|---|---|---|
| Eigenvalue (n) | Re ($\Lambda_n$) mean, μ | Re ($\Lambda_n$) std. dev., σ | Im ($\Lambda_n$) mean, μ (Hz) | Im ($\Lambda_n$) st. dev., σ (Hz) |
| 1 | −5.65 | 0.25 | 401. | 0.311 |
| 2 | −20.9 | 3.21 | 848. | 5.53 |
| 3 | −21.0 | 2.68 | 1230. | 17.2 |

TABLE 2

| | Computed System Damping | | |
|---|---|---|---|
| Eigenvalue (n) | Frequency (Hz) | Damping, c (N-sec/m) | Damping Ratio, ζ |
| 1 | 401. | 1090. | 0.042 |
| 2 | 848. | 4000. | 0.154 |
| 3 | 1230. | 4020. | 0.155 |

TABLE 3

| Comparison of Theoretical to Experimental Imaginary Natural Frequencies | | | |
|---|---|---|---|
| Eigenvalue (n) | Theoretical Frequency (Hz) | Experimental Frequency (Hz) | Percent Difference % |
| 1 | 422. | 401. | 5.0 |
| 2 | 845. | 848. | 0.4 |
| 3 | 1267. | 1230. | 2.9 |

Thus, the method described above may be used to measure frequency-dependent damping coefficients of one-dimensional devices, with a standard deviation of the damping coefficient ranging from 4.5 to 15.4 percent, according to the above-described example. The average deviation between the magnitude of the measured transfer function and the magnitude of the theoretical transfer function of 7.2 percent indicates a very stable measurement method.

It is to be understood that the present invention is by no means limited to the particular steps herein disclosed and/or illustrated in the drawings, but also comprises any modifications or equivalents within the scope of the claims.

What is claimed is:

1. A method for determining damping coefficients of viscous dampers, said method comprising the steps of:

providing a damper assembly including a bar of known length (L, in m), cross-sectional area (A, in m$^2$), density (p, in kg/m$^3$), and modulus of elasticity (E, in N/m$^2$), and a viscous damper, wherein a first end of said bar is mounted in said viscous damper while a second end of said bar is free;

applying a known force (F, in N) to said second end of said bar in a direction toward said first end of said bar;

measuring a frequency response function of the assembly, the frequency response function comprising the ratio of the bar acceleration to the applied force;

determining eigenvalues of said response function; and computing the damping coefficient (c, in N-sec/m) of said viscous damper in accordance with the formula:

$$c = \frac{AE}{s} \left\{ \frac{1 - \exp\left( \frac{2L}{s} Re(\Lambda_n) \right)}{1 + \exp\left( \frac{2L}{s} Re(\Lambda_n) \right)} \right\}$$

wherein s is the longitudinal wave speed in the bar (m/s) and $\Lambda_n$ is one of the eigenvalue.

2. The method in accordance with claim 1 wherein said application of force to said second end of said bar is provided by an impact hammer containing a force transducer for determining said applied force, and said bar acceleration is measured by an accelerometer, signals from said transducer and said accelerometer being fed to a dual channel spectrum analyzer for said measurement of said frequency response function.

3. The method in accordance with claim 2 wherein said analyzer determines said eigenvalues of said frequency response function.

* * * * *